United States Patent
Jacobs

[11] Patent Number: 5,893,855
[45] Date of Patent: Apr. 13, 1999

[54] SURGICAL STAPLER

[76] Inventor: Robert A. Jacobs, 99 Cliff Rd., Belle Terre, N.Y. 11777

[21] Appl. No.: 08/844,192

[22] Filed: Apr. 18, 1997

[51] Int. Cl.$^6$ .................................................. A61B 17/04
[52] U.S. Cl. ........................ 606/150; 606/219; 606/213
[58] Field of Search ................................. 606/149, 150, 606/219, 144, 139, 213

[56] References Cited

U.S. PATENT DOCUMENTS

| | | | |
|---|---|---|---|
| 4,471,781 | 9/1984 | Di Giovanni et al. | 128/334 R |
| 4,506,669 | 3/1985 | Blake, III. | |
| 5,282,810 | 2/1994 | Allen et al. | 606/150 |
| 5,423,856 | 6/1995 | Green. | |

Primary Examiner—Michael Buiz
Assistant Examiner—Tina T. D. Pham
Attorney, Agent, or Firm—Collard & Roe, P.C.

[57] ABSTRACT

An improved surgical stapler for closing wounds, having an approximation device connected to a side of the surgical stapler. The approximation device is a hook positioned adjacent the stapled ejection port and is adapted to grip one side of a wound and enable the operator to temporarily close the wound, while precisely positioning the staple ejection port over the closed wound. Subsequent actuation of the stapler causes the wound to be precisely stapled closed. In an alternative embodiment, the approximation device is integrally formed from one leg of a surgical staple, and provides an asymmetric staple configuration. The longer staple leg is designed with a hook end. When the stapler is partially actuated, the staple legs partially protrude from the staple ejection port, and the longer staple leg can engage the skin on one side of a wound, and enable the temporary closing of the wound for accurate positioning.

3 Claims, 4 Drawing Sheets

SURGICAL STAPLER

BACKGROUND OF THE INVENTION

1. Field of the Invention

The present invention relates to surgical staplers. More particularly, it relates to a combined surgical stapler and skin approximator for surgically stapling wounds.

2. The Prior Art

U.S. Pat. No. 5,423,856 to Green, discloses an apparatus and method for subcuticular stapling of body tissue. The invention consists of a surgical apparatus having a pair of jaws that are movable towards and away from each other, body tissue engaging pointed members extending from each jaw toward the opposing jaw, and staple means for attaching the two skin portions. The tissue engaging pointed members at the end of the device engage the tissue (skin) on opposite sides of the opening (wound or surgical), and upon closing of the jaws, causes the tissue to be drawn together and close the opening. Once drawn together, the tissue is forced into an irregular or undulating shape as a result of the pointed members. A staple or elongated attaching member is then inserted so as to attach the end portions of the body tissue.

U.S. Pat. No. 4,506,669 to Blake, III, discloses a skin approximator. The invention consists of a hinged device having two oppositely disposed arms. At the end of each arm are a pair of barbs for engaging the skin on opposite sides of a wound. Once engaged, the opposite sides of the wound are drawn together through the hinged motion of the arm, and the wound can be stapled or sutured.

The prior art devices work well for their intended purpose, but require the use of two hands to accomplish surgical stapling. Generally, one hand controls a skin approximator to draw the skin together and the other hand actuates the stapler to staple the wound. Green discloses the use of a skin approximator that can be operated with one hand to engage both opposite sides of the wound; however, a second hand is required to insert a staple-like nail to hold the two opposing edges of the wound together.

SUMMARY OF THE INVENTION

It is therefore an object of the present invention to provide a surgical stapler that can be used to draw the edges of the skin together and apply a staple using only one hand.

It is another object of the invention to provide a surgical stapler that operates efficiently and reliably.

These and other objects of the invention are accomplished by a surgical stapler having a housing, an actuator handle and means for ejecting a surgical staple from the housing by applying pressure to the actuator handle. The stapler is also equipped with a skin approximator disposed on the front or a side of the housing near the staple ejection point. The skin approximator is a device capable of grabbing and holding onto the skin edge on one side of a wound. According to a preferred embodiment of the invention, the skin approximator takes the form of a retractable hook.

When the device is in use, the surgeon uses the hook to grip the skin on one side of a wound and pull that skin towards the other side of the wound until it reaches a point where the wound is substantially closed. At this point the legs of a surgical staple may be precisely positioned over the wound such that when the actuator handle is depressed, the wound is accurately stapled closed. The entire process requires the use of only one hand, leaving the surgeon's other hand free to perform other tasks.

In an alternative embodiment, the staple itself is equipped with a skin approximator to bring the edges of the wound together prior to stapling. The staple is asymmetrical, and has an extended hook-like end on one of its legs. To use this device, the actuator handle on the stapler is partially depressed, so that the staple legs partially protrude from the staple ejection port. At this point, the longer leg of the staple, which has the hook-like end, can be used to grab the skin on one side of the wound and pull it toward the skin on the other side of the wound.

After the sides of the wound are pulled together to close the wound, the actuator handle can then be fully depressed to staple the wound closed. In this embodiment, the stapler can be similar to conventionally-used surgical staplers, but the staple chamber must be adapted so that it can accommodate the asymmetric staples.

BRIEF DESCRIPTION OF THE DRAWINGS

Other objects and features of the present invention will become apparent from the following detailed description considered in connection with the accompanying drawings which disclose an embodiment of the present invention. It should be understood, however, that the drawings are designed for the purpose of illustration only and not as a definition of the limits of the invention.

In the drawings, wherein similar reference characters denote similar elements throughout the several views.

DETAILED DESCRIPTION OF PREFERRED EMBODIMENTS

Figure 1:
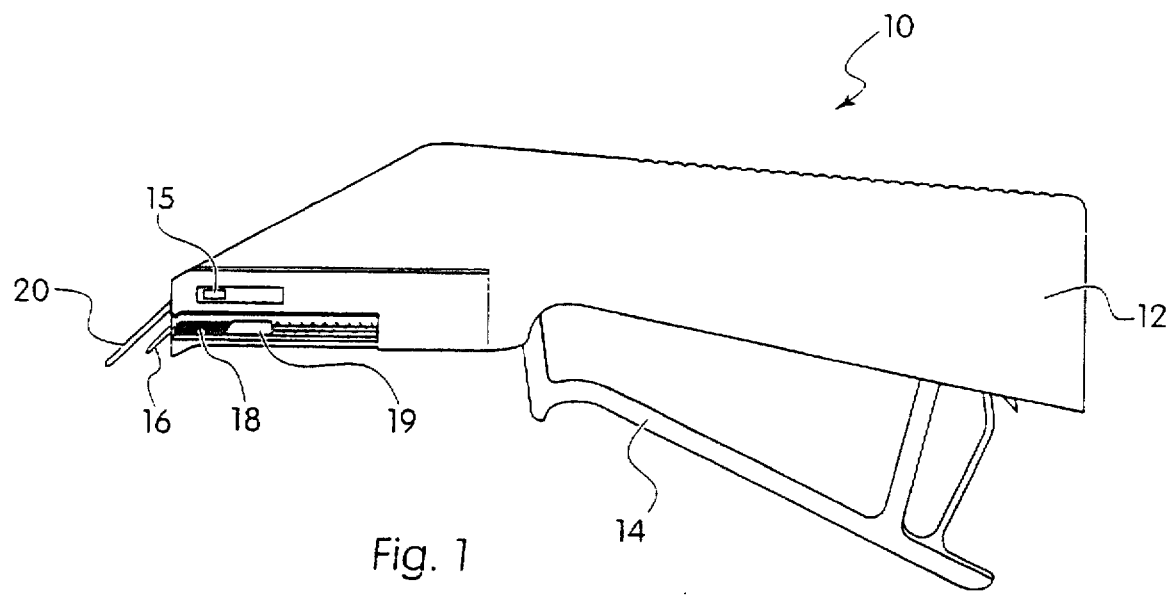
FIG. 1 is a side view of a first embodiment of the surgical stapler according to the invention.
Figure 2:
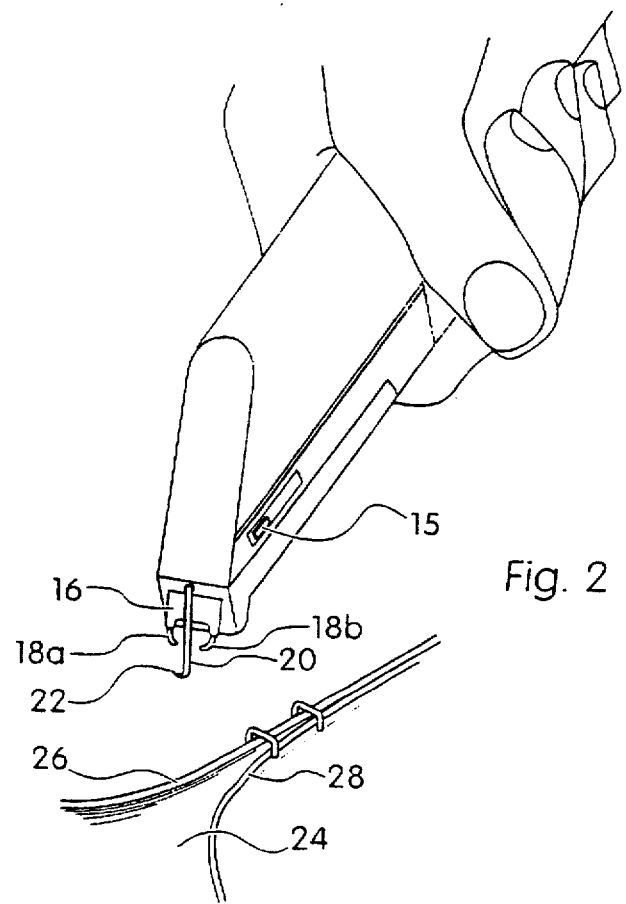
FIG. 2 is a front perspective view of the surgical stapler according to the invention.

Turning now in detail to the drawings, FIG. 1 shows a side view of the surgical stapler 10 according to the invention. Stapler 10 is has a housing 12, an actuator handle 14, and a spring loaded staple chamber 19. A plurality of staples 18 are stored inside staple chamber 19 and are biased toward the front of stapler 10 by a spring. Depression of actuator handle 14 causes one staple 18 to be ejected through an ejection port 16, as shown in FIG. 2. A switch 15 disposed on the side of stapler 10 allows hook 20 to be retracted into the stapler when not in use. Any suitable know retraction mechanism can be incorporated for this feature.

Stapler 10 has an approximator device that is essentially a hook 20 arranged on the front of housing 12, and near ejection port 16. As shown in FIG. 2, hook 20 has a pointed end 22 that can be used to engage and grab the inside of skin edge 28 on one side of a wound 24. Once engaged, skin edge 28 can then be pulled across wound 24 to meet the opposing skin edge 26.

Staple 18, which has legs 18a and 18b, is ejected from ejection port 16 when handle 14 is depressed. A partial depression of handle 14 allows legs 18a and 18b to partially protrude downward from stapler 10 without being completely ejected.

Figure 3:
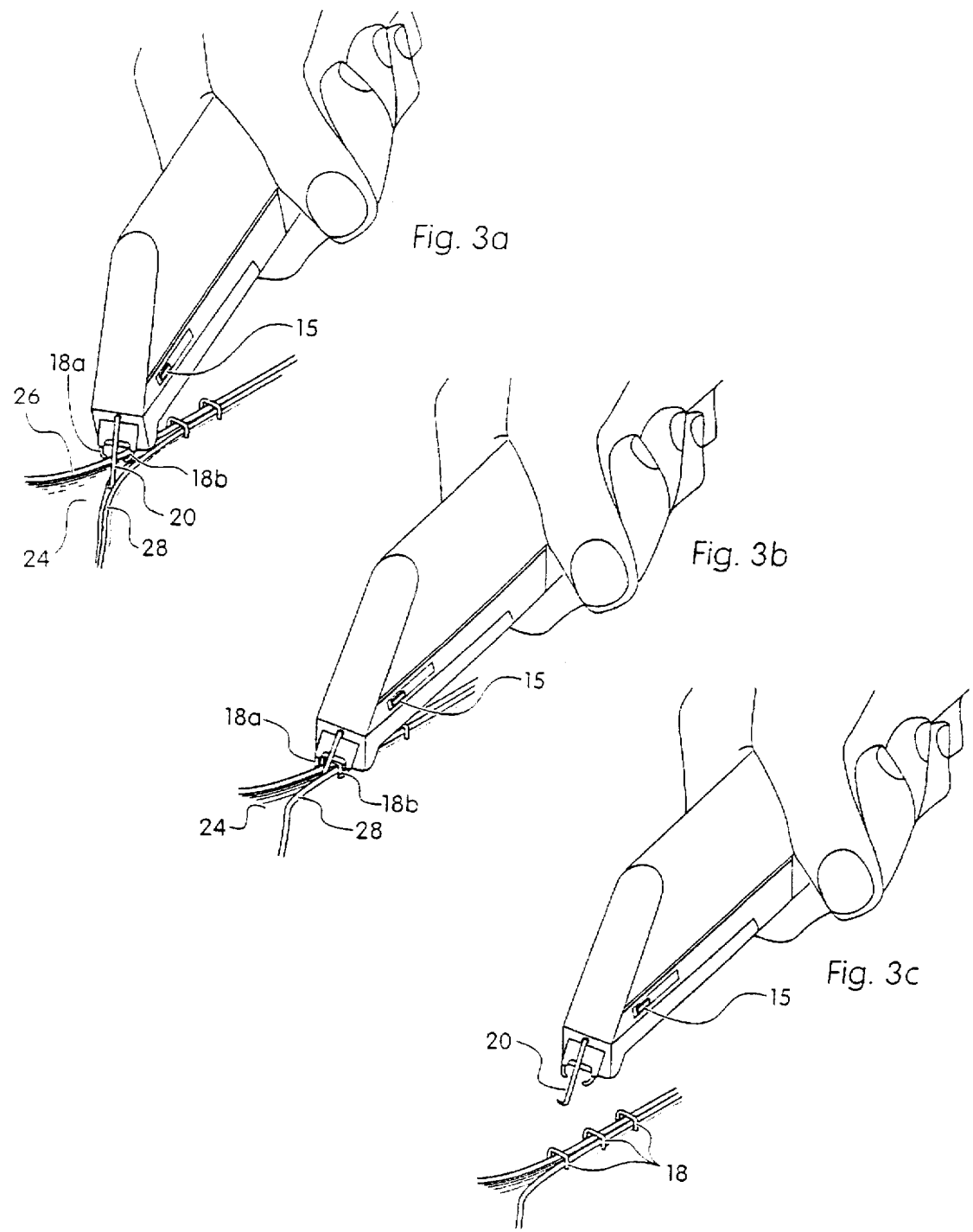
FIGS. 3a–3c show perspective views of the surgical stapler according to the first embodiment of the invention as it is used to close a wound.

FIGS. 3a–3c show stapler 10 as it is used to close a wound. First, stapler 10 is lowered so that it is near wound 24. The end 22 of hook 20 is then placed within wound 24 near edge 28 to grab the skin and pull it across the wound toward opposing edge 26. Pointed end 22 engages the wound edge in a downward hook action that requires the user to slightly rotate stapler 10 (clockwise) such that end 22 internally grips edge 28 of wound 24. As stapler 10 is rotated back (counter-clockwise) to its substantially vertical position over the wound, end 22, of hook 20, will hook onto the internal side of edge 28 and enable the user to pull edge 28 toward edge 26. This engagement of hook 20 with the internal side of edge 28 increases the user's ability to accurately position the stapler over the wound. Furthermore, the internal engagement with the wound eliminates the possibility of additional scarring or irritation of the skin around wound 24 caused from other externally engaging approximation devices.

When edges 28 and 26 are sufficiently close to each other, the user can precisely approximate the staple's position over the wound by using staple legs 18a and 18b. Once positioned over the temporarily closed wound, handle 14 is then completely depressed and legs 18a and 18b of staple 18 are inserted through edges 26 and 28 respectively, to surgically close wound 24. Once the stapling is complete, hook 20 can be carefully removed from the wound using retraction switch 15, or can be removed by pulling the extended hook from the wound by raising the stapler.

The entire process can be repeated along the entire length of wound 24 to close the wound with a series of staples 18.

Figure 4:
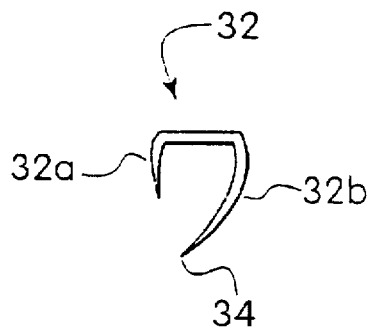
FIG. 4 is a side view of an alternative embodiment of a surgical stapler and staple according to the invention.
Figure 5:
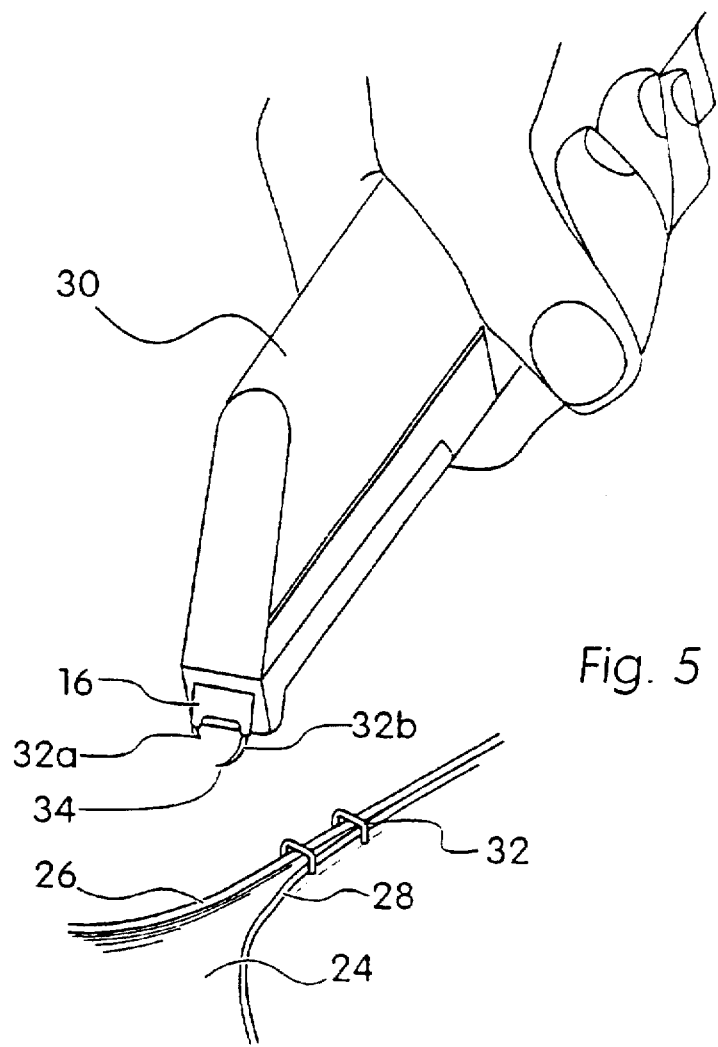
FIG. 5 is a perspective view of the surgical stapler and staple shown in FIG. 4, as they are used to close a wound.

FIGS. 4 and 5 show an alternative embodiment of the invention. In this embodiment, stapler 30 operates in the same manner as stapler 10, however, stapler 30 does not include a skin approximator 20 on the stapler itself. Instead, each staple 32 is designed asymmetrically such that it can act as a skin approximator to close the wound prior to stapling.

Staple 32 has two asymmetric legs 32a and 32b where leg 32b functions as a skin approximator by including a hook end 34. During use, stapler 30 is placed near wound 24 and actuator handle 14 is partially depressed so that legs 32a and 32b of staple 32 partially protrude from ejection port 16. At this point, hook 34 can be used to grab edge 28 and pull it toward edge 26. Once the edges are aligned, actuator handle 14 is fully depressed, and staple legs 32a and 32b are inserted into edges 26 and 28 to close wound 24.

This process can be repeated for all staples 32 in stapler 30. Stapler 30 is similar in structure and operation to conventionally used surgical staplers, however staple chamber 19 is specially adapted to accommodate asymmetric staples 32 with the built-in skin approximator 34.

Figures 6A, 6B:
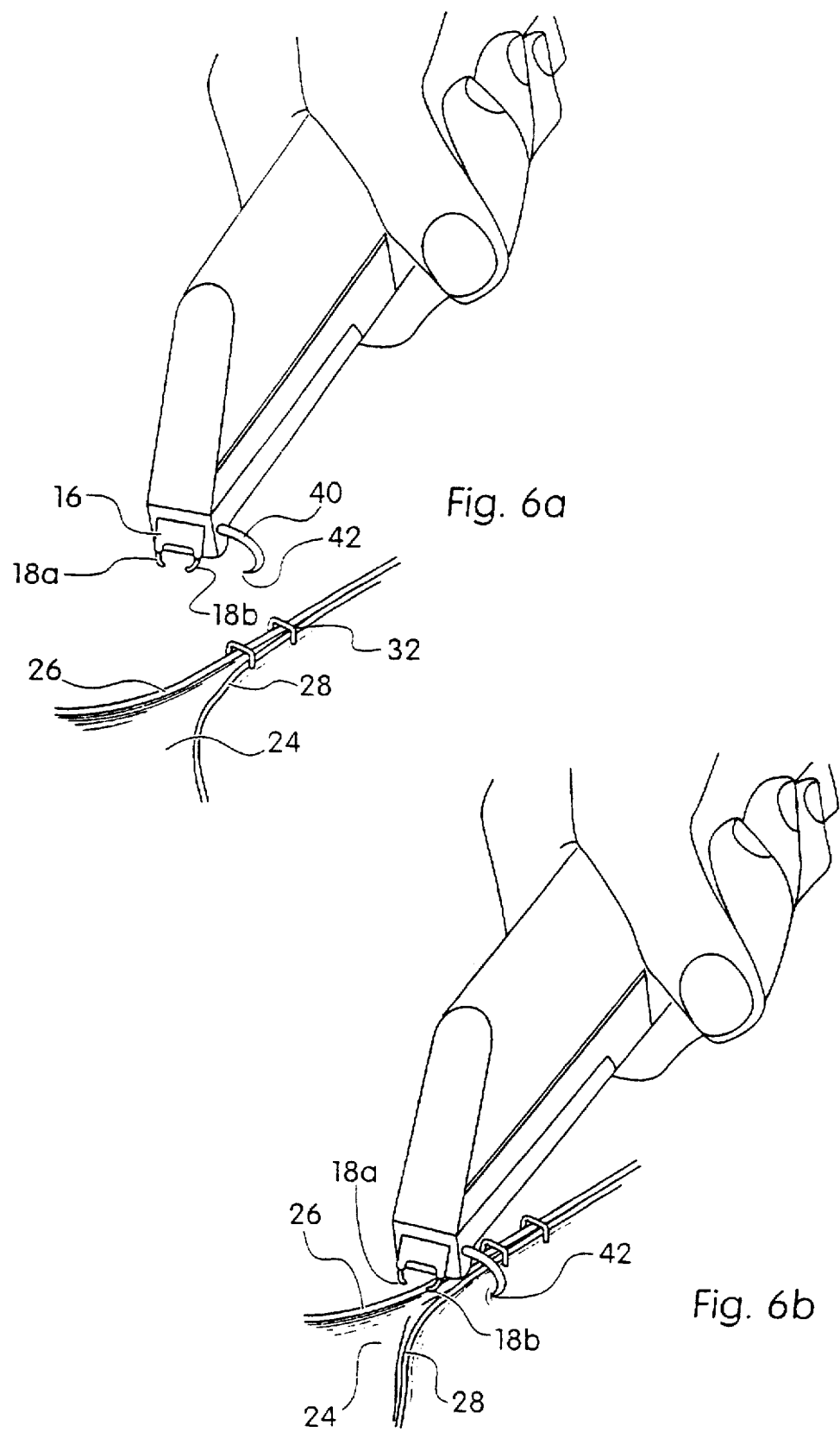
FIG. 6a is a perspective view of a third embodiment of the surgical stapler according to the invention.
FIG. 6b is a perspective view of the third embodiment of the surgical stapler as is it used to close a wound.

FIGS. 6a and 6b show an alternative embodiment of the surgical stapler with a hook 40 extending from a side of the stapler. Hook 40 has a pointed end 42 for engaging the skin near edge 28 and enabling the user to pull edge 28 over to edge 26 to position staple legs 18a and 18b over the wound for stapling. In this embodiment, hook 40 engages the skin on the outside of the wound.

While several embodiments of the present invention have been shown and described, it is to be understood that many changes and modifications may be made thereunto without departing from the spirit and scope of the invention as defined in the appended claims.

What is claimed is:

1. An improved surgical stapler for closing wounds and having a housing, an actuator handle, a staple ejection port at the front, and a staple chamber for receiving surgical staples, comprising:

a skin approximation device in the form of a single hook directly connected to the surgical stapler housing and being adapted to grip one side of an open wound.

2. The surgical stapler according to claim 1, further comprising a retraction mechanism connected to said skin approximation device for retracting the approximation device into the stapler.

3. The surgical stapler according to claim 1, wherein said skin approximation device has a free end disposed parallel to and substantially centered with respect to the staple ejection port of the stapler for engaging one side of the open wound and enabling the operator to close the wound and position the staple ejection port over the closed wound.

* * * * *